(12) United States Patent
Rolle

(10) Patent No.: US 10,124,123 B2
(45) Date of Patent: Nov. 13, 2018

(54) REUSABLE SYRINGE

(71) Applicant: Transcodent GmbH & Co. KG, Kiel (DE)

(72) Inventor: Philipp Rolle, Neumünster (DE)

(73) Assignee: TRANSCODENT GMBH & CO. KG, Kiel (DE)

( * ) Notice: Subject to any disclaimer, the term of this patent is extended or adjusted under 35 U.S.C. 154(b) by 261 days.

(21) Appl. No.: 14/897,972

(22) PCT Filed: Jun. 11, 2014

(86) PCT No.: PCT/EP2014/062123
§ 371 (c)(1),
(2) Date: Dec. 11, 2015

(87) PCT Pub. No.: WO2014/198769
PCT Pub. Date: Dec. 18, 2014

(65) Prior Publication Data
US 2016/0136361 A1     May 19, 2016

(30) Foreign Application Priority Data

Jun. 13, 2013  (EP) ..................... 13171882

(51) Int. Cl.
*A61M 5/34* (2006.01)
*A61M 5/24* (2006.01)

(52) U.S. Cl.
CPC .............. *A61M 5/347* (2013.01); *A61M 5/24* (2013.01); *A61M 5/344* (2013.01); *A61M 5/348* (2013.01);
(Continued)

(58) Field of Classification Search
CPC ........ A61M 5/347; A61M 5/24; A61M 5/344; A61M 5/348
See application file for complete search history.

(56) References Cited

U.S. PATENT DOCUMENTS 2,517,689 A   8/1950   Lement
2,604,890 A   7/1952   Burnside
(Continued)

FOREIGN PATENT DOCUMENTS

DE   202004018738 U1   4/2005
EP       0787501 A2   8/1997

OTHER PUBLICATIONS

Definition of Inclined (Merriam-Webster May 18, 2018).*
International Search Report dated Nov. 6, 2015 (PCT/EP2014/062123).

*Primary Examiner* — Nathan R Price
*Assistant Examiner* — Dung Ulsh
(74) *Attorney, Agent, or Firm* — Global IP Counselors, LLP

(57) ABSTRACT

The invention relates to a reusable syringe with a syringe body for receiving an ampoule. At the front end of the syringe body there is an opening which defines an axis along which a needle can be inserted. A plurality of holding segments are arranged around this axis and engage behind a needle carrier in the longitudinal direction. According to the invention, a holding segment designed as a thread part is movable in the radial direction. The invention further relates to a system composed of a reusable syringe, a needle carrier, and a container for used needles. Moreover, the invention includes an associated method for connecting and releasing a needle of a reusable syringe. The movable holding segment facilitates the release of the threaded connection of the needle carrier from the syringe body and makes the reusable syringe safer to use.

15 Claims, 4 Drawing Sheets

(52) U.S. Cl.
CPC ... *A61M 2205/581* (2013.01); *A61M 2207/00* (2013.01)

(56) References Cited

U.S. PATENT DOCUMENTS

| | | |
|---|---|---|
| 3,063,450 A | 11/1962 | Myerson et al. |
| 2003/0163093 A1* | 8/2003 | Thibault ............... A61M 5/344 604/241 |
| 2004/0054336 A1* | 3/2004 | Klint .................... A61M 5/347 604/272 |
| 2004/0064108 A1 | 4/2004 | Krantz et al. |
| 2008/0086092 A1 | 4/2008 | Loe |
| 2009/0318877 A1* | 12/2009 | Korn ................... A61M 5/3213 604/198 |
| 2011/0288493 A1* | 11/2011 | Holmqvist ............ A61M 5/24 604/241 |
| 2013/0102973 A1* | 4/2013 | Thorley ................. A61M 5/34 604/240 |
| 2013/0231614 A1* | 9/2013 | Cross .................. A61M 5/3134 604/198 |
| 2013/0245561 A1* | 9/2013 | Kouyoumjian ......... A61M 5/20 604/191 |
| 2013/0274679 A1* | 10/2013 | Jugl ...................... A61M 5/347 604/201 |
| 2013/0331799 A1* | 12/2013 | Dasbach ............... A61M 5/321 604/241 |
| 2014/0039413 A1* | 2/2014 | Jugl ..................... A61M 5/346 604/240 |
| 2014/0094758 A1* | 4/2014 | Jugl .................... A61M 5/3202 604/198 |
| 2015/0011936 A1* | 1/2015 | Okihara ................ A61M 5/344 604/111 |
| 2016/0151581 A1* | 6/2016 | Giambattista ..... A61M 5/31536 604/189 |

* cited by examiner

REUSABLE SYRINGE

BACKGROUND

The invention relates to a reusable syringe with a syringe body for receiving an ampule. An opening is arranged at the front end of the syringe body and defines an axis along which a needle can be inserted. A plurality of holding segments are arranged around this axis and are configured to engage with a needle carrier.

Reusable syringes of this kind can be used to inject a liquid, for example a medicament or an anesthetic, into a patient. Unlike conventional disposable syringes, the reusable syringe has an ampule which is prefilled with the liquid to be injected and which is inserted into the seat of the syringe body. The rear end of a needle secured on the needle carrier is then inserted into the opening arranged at the front end of the syringe body, to such an extent that the rear end of the needle pierces a membrane on the front face of the ampule. A mating thread of the needle carrier is screwed onto the corresponding thread of the syringe body. In this procedure, a protective cap is usually provided which is mounted on the front end of the needle carrier. It protects a user from needlestick injuries, which can arise if the sharp needle is touched.

After the injection, the needle has to be disposed of together with the needle carrier connected to it. Reusable syringes known from the prior art have the disadvantage that the needle carrier first has to be unscrewed from the syringe body in order to be disposed of. During the unscrewing procedure, there is a high risk of injury, since an operator, with a hand in direct proximity to the unprotected needle, has to apply a certain unscrewing force and, in doing so, the hand can slip. Alternatively, a protective cap can again be mounted on the needle prior to the unscrewing procedure. However, the procedure of re-capping the protective cap, referred to as recapping, can also entail a high risk of needlestick injuries.

SUMMARY

The object of the present invention is to make available a reusable syringe which is more user friendly and safer. Proceeding from the stated prior art, the object is achieved by the features of independent claim 1. Advantageous embodiments are set forth in the dependent claims. According to the invention, provision is made that a holding segment configured as a thread part is movable in the radial direction.

First, a number of terms used in the context of the invention are defined. A reusable syringe designates, in the context of the invention, a syringe in which the syringe body can be used a number of times. In such a syringe, the ampule and the needle carrier with the connected needle can be connected to the syringe body before each use. The reusable syringe can be a barrel ampule syringe, for example.

The opening arranged at the front end of the syringe body defines a longitudinal axis. A radially directed axis lies perpendicular to this longitudinal axis and intersects the longitudinal axis.

The needle can be connected to the reusable syringe via the needle carrier. The needle is preferably firmly connected to the needle carrier.

By means of a holding segment being movable in the radial direction, the release of the needle carrier from the syringe body is made much easier. When the movable holding segment, which is in engagement with the needle carrier, is moved in the radial direction, the movable holding segment is released from the needle carrier and the engagement with the needle carrier is canceled. The needle carrier is in this way no longer securely held and can easily be pulled off in the longitudinal direction, without a rotation movement, for example, having to be effected for the release. For example, the needle carrier can be pulled off with the aid of a needle waste container. The needle carrier can for this purpose be inserted into a matching opening of the needle waste container. After a form-fit connection has been produced between the needle carrier and the boundary of the opening of the needle waste container, the needle carrier can then be pulled off in the longitudinal direction. The disposal of the needle carrier and of the connected needle is thus made considerably safer and easier.

It is also possible for a plurality of holding segments to be movable in the radial direction. Preferably, all the holding segments are movable in the radial direction. All the holding segments can then be released from the needle carrier without said needle carrier having to be moved in the radial direction. The needle carrier can be configured such that, when all of the holding segments are released, it is held only by the rear end of the needle that is inserted into the membrane of the ampule. The removal and disposal of the needle carrier in a needle waste container is in this case particularly easy and safe.

The holding segments can have projections which are directed in the radial direction and which are designed to engage behind the needle carrier such that the needle carrier cannot be pulled off in the longitudinal direction. Preferably, the radial projections form a thread structure, such that the holding segments are configured as thread parts. The thread structure is preferably shaped such that the thread structures of a plurality of thread parts form segments of a common thread when the holding segments are in the engagement position in which they can be brought into engagement with the needle carrier. The thread structure thus differs from a normal continuous thread only in terms of interruptions between the thread segments. The thread is preferably a standard thread, for example a metric thread or an imperial thread. This configuration of the holding segments as thread parts permits a secure hold of the needle carrier on the syringe body. Moreover, the reusable syringe is in this way compatible with conventional needle carriers.

The syringe according to the invention can comprise a needle connected to a needle carrier, wherein the needle carrier has a mating thread matching the thread formed by the holding segments. The thread formed by the holding segments is configured for engagement with the mating thread.

In a preferred embodiment, free spaces are arranged between the holding segments. The free spaces permit a radially inwardly directed movement of the holding segments, without the holding segments abutting each other. The reusable syringe preferably has three holding segments. The use of three holding segments firstly permits a secure hold of the needle carrier when the latter is connected to the holding segments. Secondly, however, the holding segments can be easily released from the needle carrier during a movement of one or more of said holding segments.

In a preferred embodiment, the movable holding segment is provided with a guide surface. A guide element is preferably provided which is movable in the longitudinal direction relative to the syringe body and which moves the guide surface and therefore the holding segment in the radial direction during a longitudinal movement of the guide surface. It is advantageous if the guide element is arranged around the syringe body. Such a guide element can be operated easily, for example even with just one hand, and thus permits a particularly simple movement of the holding segments. The guide element can also comprise an inner thread, which interacts with a corresponding outer thread of the syringe body. Preferably, the guide element is moved in the longitudinal direction during a rotation about the longitudinal axis of the syringe body. This embodiment can likewise be operated with one hand. Preferably, an individual guide element is configured to move all of the movable holding segments.

Provision can be made that the guide element limits the inward and outward mobility of the holding segments. Alternatively, a resetting element can be provided which presses the guide surface radially against the guide element. It is then not necessary that the guide element acts on the holding segments both from the inside and also from the outside.

The movable holding segment is preferably movable between an outer position and an inner position. The outer position corresponds to a position of the guide element in which the guide surfaces lie farthest to the outside. The outer position can be defined by the guide element limiting the outward movement or by the inwardly pressing resetting element. The inner position corresponds to a position of the guide element in which the guide surfaces lie farthest to the inside. The inner position can be defined by the guide element limiting the inward movement or by the outwardly pressing resetting element. The holding segments preferably engage behind the needle carrier in the outer position. In the inner position, the holding segments are preferably released from the needle. This applies when using a needle carrier that can be engaged from behind on the inside. However, it is also conceivable to use a needle carrier that can be engaged from behind on the outside. In this case, the holding segments engage behind the needle carrier in the inner position and are released from the needle carrier in the outer position. The operation of the reusable syringe is simplified by the fact that there are two defined positions.

The guide element preferably comprises an oblique surface, which encloses an angle with the longitudinal axis of the syringe body. The guide surface of the holding segment is preferably configured as a corresponding oblique surface. The oblique surface of the guide element can bear on the guide surface. By means of a movement of the guide element relative to the syringe body, the guide surface is able to slide along the oblique surface. On account of the angle between the oblique surface and the longitudinal axis, the guide surface and the movable holding segment secured thereon are moved in the radial direction. To ensure that the longitudinal movement of the guide element is converted into a radial movement of the holding segments, the holding segments are preferably held in a fixed longitudinal position relative to the syringe body.

The holding segments can be parts that are separate from the syringe body and that are held only by suitable guide surfaces in a defined position relative to the syringe body. Alternatively, the holding segments can be connected to the syringe body via elastic connection parts. The necessary mobility of the holding segments in the radial direction can then come from the elastic connection parts.

As a result of the inward movement of the holding segments, the space lying between the holding segments becomes smaller at the front end of the syringe body. Preferably, the space has a diameter which is greater than the diameter of the needle when the holding segments are located in the inner position. For example, the diameter of the space can be greater than 0.5 mm when the holding segments are located in the inner position. This ensures that the rear end of the needle can in each case be inserted into the opening of the syringe body.

It is advantageous if the guide element latches in place when it reaches the inner position and/or the outer position. Provision can also be made that the guide element can be locked when it reaches one of the two positions, i.e. inner position and outer position. Latching or locking of the guide element ensures that the guide element and the holding segments connected thereto remain in the desired position. Thus, for example, unwanted release of the needle carrier is prevented. It is also advantageous if an acoustic signal is emitted when the guide element is locked or latched in place. The acoustic signal can be a click, for example. The operator is thus provided with an audible indication that the desired position has been reached or that locking has taken place, and the operation is thus further facilitated.

The present invention further relates to a system comprising a reusable syringe and a needle carrier with a needle. The needle carrier can be brought into engagement with the holding segments of the reusable syringe. The connection is such that, when the needle carrier is in engagement, the needle pierces an ampule received by the syringe body. The system can moreover comprise a needle waste container, which is configured to engage behind the needle carrier. When the needle carrier is in engagement with this structure, the needle carrier can be released from the syringe body if the engagement of the holding segments has been released. For this purpose, the syringe body is pulled away in the longitudinal direction from the waste container. The waste container can comprise a collecting space arranged below the structure, into which collecting space the needle carrier drops with the needle as soon as the syringe body has been pulled off. Before the use of the reusable syringe, the needle carrier can be secured on the syringe body with the aid of the holding segment.

The present invention moreover relates to a method for connecting and releasing a needle of a reusable syringe. The reusable syringe comprises a syringe body and a needle carrier connected to a needle. The syringe body is provided with a holding segment designed as a thread part. The needle carrier comprises a mating thread matching the holding segment. In the method, the mating thread of the needle carrier is screwed onto the thread part of the holding segment. The holding segment is moved in the radial direction. By means of the movement of the holding segment, the latter is released from engagement with the needle carrier. The needle carrier can be pulled off from the syringe body. This can be done, for example, by the needle carrier being inserted into an opening of a needle waste container such that a form-fit connection with said structure of the needle waste container is obtained. After it has been pulled off, the needle carrier, with the needle secured thereon, drops into the needle waste container.

The method can be developed with further features, which are described in the context of the reusable syringe according to the invention.

BRIEF DESCRIPTION OF THE DRAWINGS

The invention is described below on the basis of advantageous illustrative embodiments and with reference to the attached drawings, in which.

DETAILED DESCRIPTION

Figure 1:
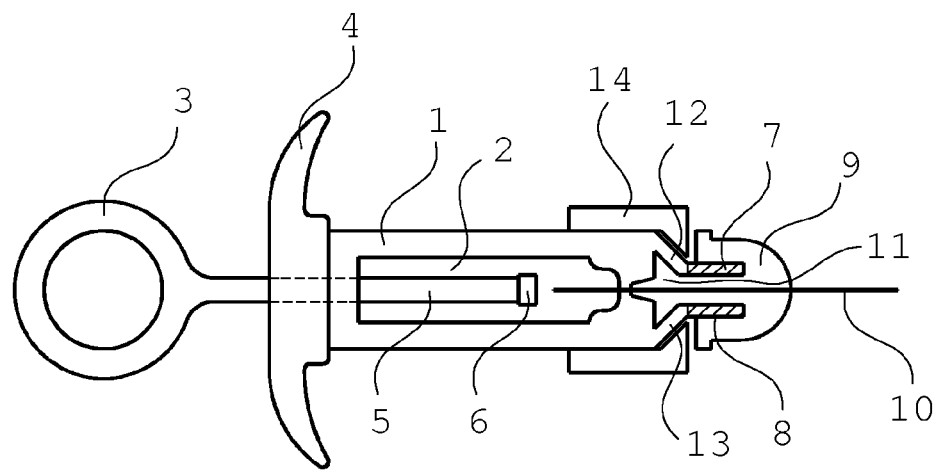
FIG. 1 shows a sectional side view of a reusable syringe according to the invention with needle carrier.

A reusable syringe according to the invention comprises a cylindrical syringe body 1, which has a substantially cylindrical ampule receiver 2. A plunger 5 is inserted into the syringe body through an opening at the rear end of the syringe body and can be moved along the longitudinal axis of the syringe body 1. A thumb ring 3 is arranged at the rear end of the plunger 5, while a ram 6 is located at the front end of the plunger. Moreover, at the rear end of the syringe body 1, there is a handle 4 which, in interaction with the thumb ring 3, allows the reusable syringe to be easily operated.

Figure 6:
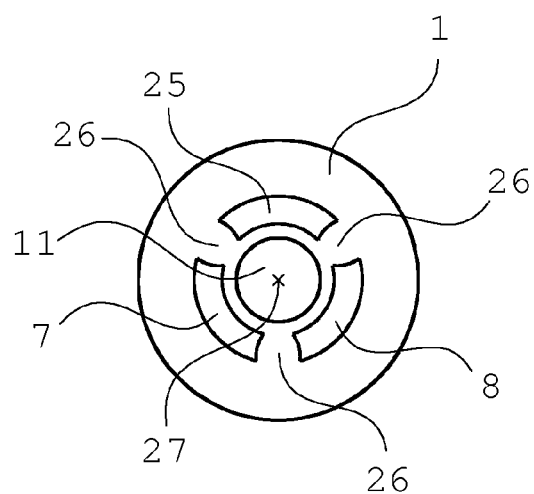
FIG. 6 shows a view, in the longitudinal direction, of the front end of a reusable syringe according to the invention.

Arranged at the front end of the syringe body 1 are three holding segments in the form of thread parts, of which only the two thread parts 7, 8 can be seen in the sectional side view. The thread parts 7, 8 are connected to the front end of the syringe body 1 via elastic guide surfaces 12, 13. The three thread parts are in engagement with a mating thread of a needle carrier 9. A needle 10, secured on the needle carrier 9, is inserted into the syringe body 1 through the opening 11. The opening has oblique surfaces which are inclined with respect to the longitudinal axis of the syringe body and facilitate the insertion of the needle 10. The opening 11 defines an axis, which is defined by the orientation of the needle 11 when the needle carrier is screwed onto the syringe body. The thread parts are arranged around this axis. FIG. 6 shows the arrangement of the three thread parts. The axis defined by the opening 11 corresponds to the longitudinal axis of the syringe body 1.

A barrel ampule (not shown in FIG. 1) can be inserted into the ampule receiver 2 of the syringe body 1. The front end face of the barrel ampule is usually formed by a membrane, which is pierced by the rear end of the needle 10. The ram 6 can then be moved in the direction of the inserted barrel ampule and pressed into the rear end of the barrel ampule. The liquid located in the barrel ampule then emerges from the front end of the needle 10.

In the state shown in FIG. 1, the thread parts 7, 8 are located in an outer position. In this position, the thread parts 7, 8 are in engagement with a mating thread (not shown in FIG. 1) of the needle carrier 9. By way of the guide element 14, which is arranged around the front end of the syringe body 1, the thread parts 7, 8 can be moved from the outer position to an inner position. This is explained in detail below with reference to FIGS. 2 and 3.

Figure 2:
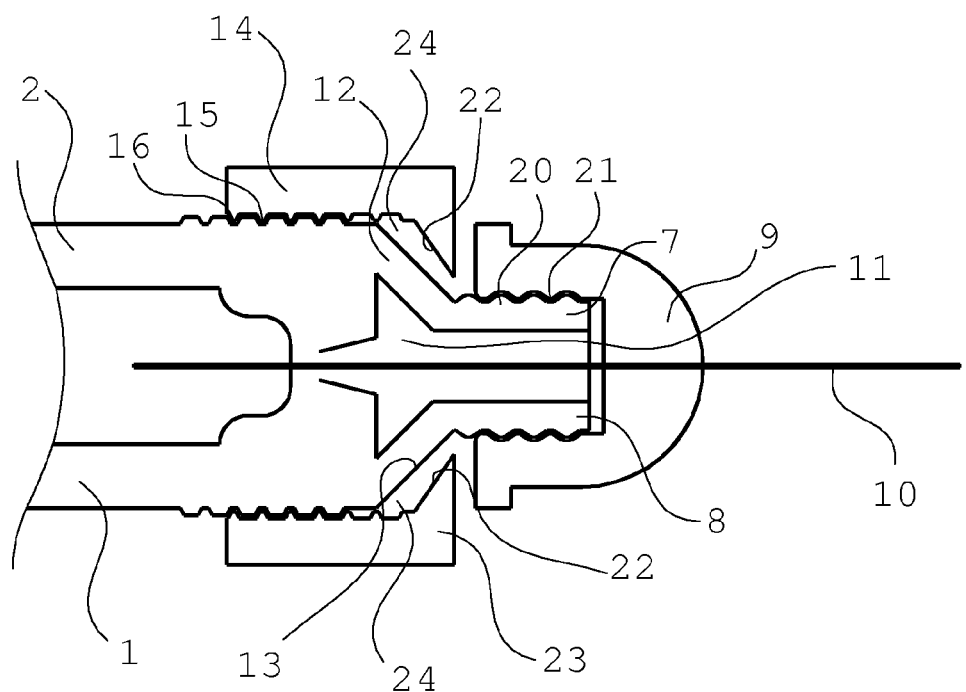
FIG. 2 shows an enlarged detail from FIG. 1.

FIG. 2 shows an enlarged view of the front end of the reusable syringe. The thread parts 7, 8 are also located in the outer position in FIG. 2. It will be seen from this view that the thread elevations 20 of the thread parts 7, 8 are in engagement with the thread depressions of the inner thread 21 of the needle carrier 9. FIG. 2 moreover shows the substantially cylindrical guide element 14, which is arranged around the front end of the syringe body 1. At the front end of the syringe body 1 there is an outer thread 16, which is in engagement with an inner thread 15 of the guide element 14. On account of the two threads 15, 16 being in engagement, the guide element 14, upon rotation about the longitudinal axis relative to the syringe body 1, executes a movement in the longitudinal direction of the syringe body 1.

The guide element 14 further comprises, at its front end, a projection 23 with a rearwardly directed oblique surface 22. In the outer position of the thread parts 7, 8 as shown in FIG. 2, a space 24 is present between the oblique surface 22 and the guide surfaces 12, 13.

Figure 3:
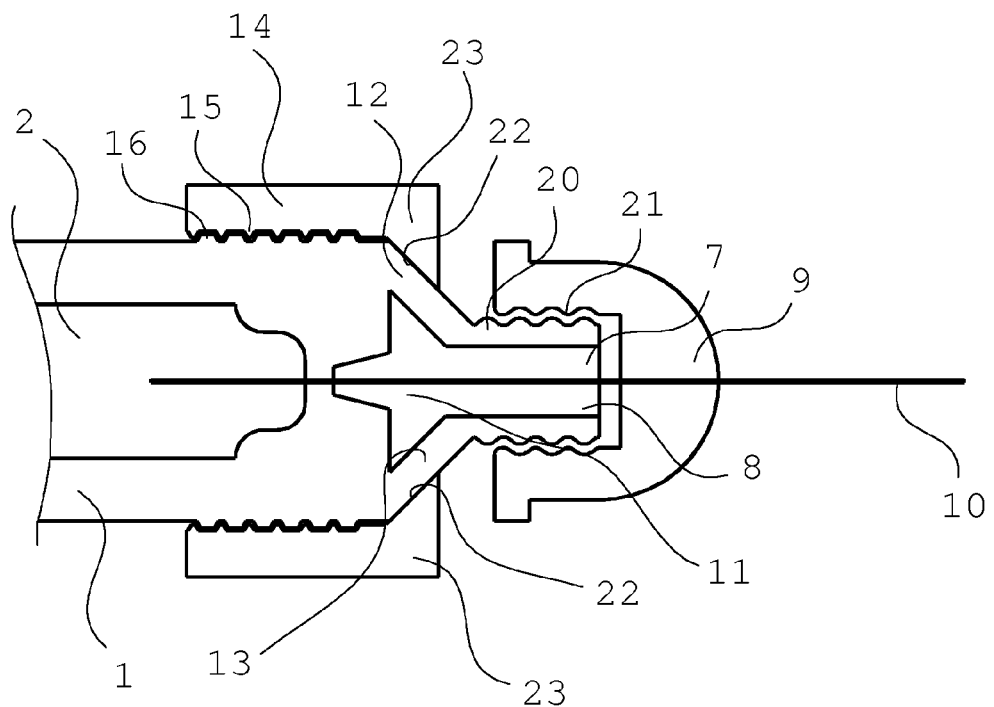
FIG. 3 shows the view from FIG. 2, with the holding segments in another state.

By a rotation of the guide element 14 about the longitudinal axis of the syringe body 1, the guide element 14 can be moved rearward relative to the syringe body 1 until the position shown in FIG. 3 is reached. By means of this movement, the oblique surfaces 22 are moved rearward, such that the free space 24 initially becomes smaller and the oblique surfaces 22 finally bear on the guide surfaces 12, 13. Upon a further relative movement, the oblique surfaces 22 exert a force on the guide surfaces 12, 13. The guide surfaces 12, 13 are elastic and are thereby deflected from the position shown in FIG. 2. While the guide surfaces 12, 13 in FIG. 2 enclose a 45° angle with the longitudinal axis of the syringe body 1, in FIG. 3 the angle is increased to 60° through the deflection of the guide surfaces 12, 13. Since the thread parts 7, 8 are connected to the guide surfaces 12, 13, the thread parts 7, 8 are moved radially inward during the deflection, shown in FIG. 3, of the guide surfaces 12, 13. In this way, the thread elevations 20 of the thread parts 7, 8 are released from the mating thread 21 of the needle holder 9. In the inner position of the thread parts 7, 8 as shown in FIG. 3, the thread elevations 20 are no longer in engagement with the mating thread 21.

To release the needle carrier 9, the latter can then be inserted into the opening 52 of a needle waste container 50, such that a form-fit connection is obtained between the structure 51 of the needle waste container 50 and the needle carrier 9. The needle carrier 9 can then be pulled easily and safely from the reusable syringe.

For renewed use of the reusable syringe, the guide element 14 can be rotated about the longitudinal axis of the syringe body until it reaches the position shown in FIG. 2. As soon as the oblique surfaces 22 no longer exert any force on the guide surfaces 12, 13, the elastic guide surfaces 12, 13 move back to the position shown in FIG. 2. The thread parts 7, 8 can then be brought into engagement again with the mating thread of a new needle carrier 9.

Figure 4:
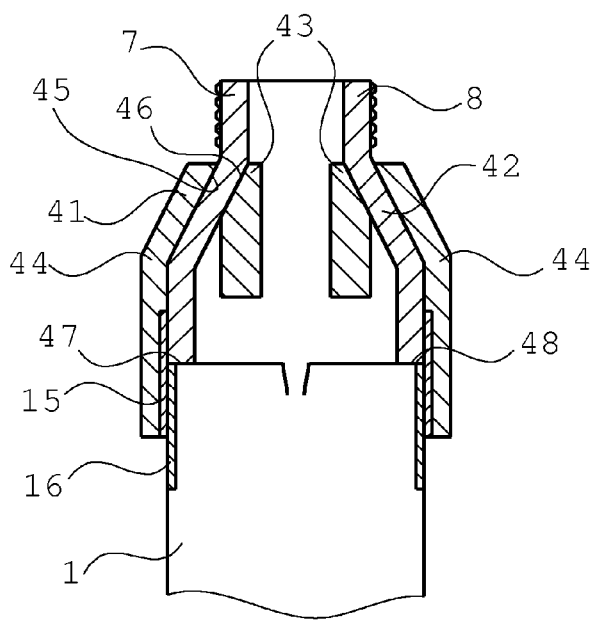
FIG. 4 shows the front part of a further embodiment of a reusable syringe according to the invention.
Figure 5:
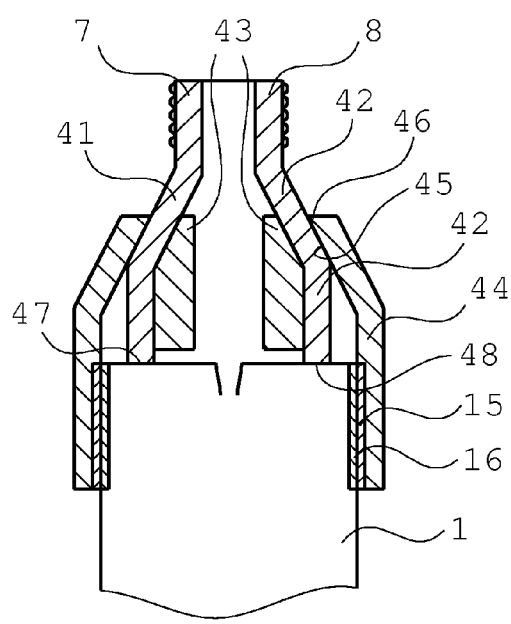
FIG. 5 shows the view from FIG. 4, with the holding segments in another state.

FIGS. 4 and 5 show a sectional view of the front part of a further embodiment of a reusable syringe according to the invention. In FIG. 4, the movable holding segments 7, 8 are located in the outer position, while in FIG. 5 they are located in the inner position. The needle carrier and the needle are not shown in FIGS. 4 and 5. In this embodiment, the guide surfaces 41, 42 are not firmly connected, at their rear end 47, 48, to the front end of the syringe body 1, and instead they bear radially movably on the syringe body. The guide surfaces 41, 42 are held between an inner part 43 of the guide element and an outer part 44 of the guide element. The parts 43, 44 of the guide element are connected rigidly to each other via a connection not shown in the sectional view. The outer guide element 44 has an oblique surface 45, which bears from outside on the guide surfaces 41, 42. The inner guide element 43 has an oblique surface 46, which bears from inside on the guide surfaces 41, 42. The oblique surfaces 45, 46 and the guide surfaces 41, 42 enclose an angle of 27° with the longitudinal axis of the syringe body 1.

Figure 7:
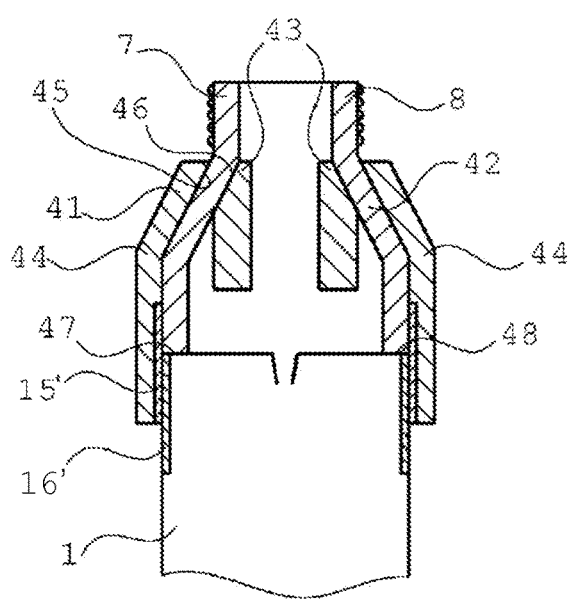
FIG. 7 shows a longitudinal sectional view of the front end of an alternative embodiment of a reusable syringe according to aspects of the disclosure.
Figure 8:
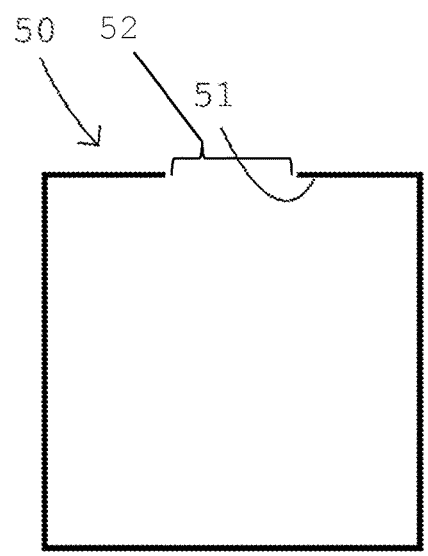
FIG. 8 shows a needle waste container according to aspects of the disclosure.

The outer part 44 of the guide element comprises an inner thread 15, which is in engagement with an outer thread 16 of the syringe body 1. Upon rotation of the guide element 43, 44 about the longitudinal axis, the guide element can be moved in the longitudinal direction relative to the syringe body in the direction of the rear end of the syringe body 1, until the position shown in FIG. 5 is reached. During this movement, the guide surfaces 41, 42 slide along the oblique surfaces 45, 46 of the guide element 43, 44. The guide surfaces 41, 42 are moved radially inward. In this way, the thread elevations 20 of the thread parts 7, 8 are released from the mating thread (not shown in FIGS. 4 and 5) of the needle carrier. An alternative embodiment of a reusable syringe shown in FIG. 7, includes a sliding guide 15', which permits sliding movement of the outer part 44 of the guide element along the corresponding guide 16' on the syringe body.

FIG. 6 shows a view, in the longitudinal direction, of the front end of the syringe body. The guide element, the guide surfaces and the needle carrier are not shown in FIG. 6. The three thread parts 7, 8, 25 are arranged around the axis 27 which is defined by the opening 11 at the front end of the syringe body 1 and which is perpendicular to the plane of the drawing. Free spaces 26 are arranged between the thread parts 7, 8, 25, such that the thread parts 7, 8, 25 do not abut each other when moved inward. The thread parts have an angular spacing of 120° in the circumferential direction, such that they are distributed uniformly about the axis 27. If the thread parts 7, 8, 25 are located in the outer position, the thread has a metric configuration.

The invention claimed is:

1. A reusable syringe comprising:
a syringe body for receiving an ampule, said syringe body defining a longitudinal axis along which a needle can be inserted into an opening defined at a front end of the syringe body, a plurality of holding segments axially projecting from said front end, said plurality of holding segments arranged around said opening and configured to engage with a needle carrier having a radially inward directed thread facing toward said longitudinal axis, wherein at least one of said plurality of holding segments includes radially outward directed projection facing away from said longitudinal axis and is movable in a radial direction, the at least one of said plurality of holding segments having a guide surface; and
a guide element surrounding said plurality of holding segments and axially movable relative to the syringe body and the needle carrier, said guide element including an inclined surface radially outward of said guide surface,
wherein movement of said guide element along said longitudinal axis toward said syringe body brings said inclined surface into contact with said guide surface and moves said at least one of said plurality of holding segments radially inwardly from a first position where said radially outward directed projection is engaged with said radially inward directed thread, to a second position where said radially outward directed projection is not engaged with said radially inward directed thread and said needle carrier can be separated from said syringe body.

2. The reusable syringe as claimed in claim 1, wherein each of the plurality of holding segments is movable in the radial direction.

3. The reusable syringe of claim 1, wherein said radially outward directed projection is a radially outward directed thread complementary to the radially inward directed thread of said needle carrier.

4. The reusable syringe as claimed in claim 1, wherein free spaces are arranged between said plurality of holding segments.

5. The reusable syringe as claimed in claim 1, wherein said plurality of holding segments comprises three holding segments.

6. The reusable syringe as claimed in claim 1, wherein the guide element comprises a thread, which interacts with a corresponding mating thread of the syringe body.

7. The reusable syringe as claimed in claim 1, wherein the guide element is in engagement with the syringe body via a sliding guide oriented in the longitudinal direction.

8. The reusable syringe as claimed in claim 1, wherein the guide element latches in place on reaching said first position and/or said second position.

9. The reusable syringe as claimed in claim 1, wherein the guide element is lockable in said first position and/or said second position.

10. The reusable syringe as claimed in claim 1, wherein said guide element is lockable and/or latchable in the first position and/or said second position and the latching and/or locking of the guide element is associated with an acoustic signal.

11. The reusable syringe as claimed in claim 3, wherein the needle is connected to the needle carrier, and the radially outward directed thread of said plurality of holding segments can be brought into engagement with the radially inward directed thread of the needle carrier when said plurality of holding segments are in said first position.

12. The reusable syringe of claim 1, wherein each of said plurality of holding segments are movable in a radial direction between said first position and said second position, and each holding segment includes a radially outward directed thread complementary to said radially inward directed thread.

13. The reusable syringe of claim 1, wherein said at least one holding segment includes a second guide surface radially opposite said guide surface, and said guide element includes structure to engage said second guide surface, thereby controlling movement of said at least one holding segment during radially inward movement and during radially outward movement.

14. A system comprising:
a reusable syringe with a syringe body for receiving an ampule, said syringe body having a longitudinal axis, a front end defining an opening into which a needle can be inserted along said longitudinal axis, and a plurality of axially projecting holding segments arranged around said opening having distal ends configured to engage with a needle carrier, said plurality of axially projecting holding segments being movable in a radial direction;
the needle carrier with said needle, the needle carrier having an inside surface for engagement by the distal ends of said plurality of axially projecting holding segments to retain said needle carrier to said syringe body;
a guide element surrounding said plurality of axially projecting holding segments and axially movable relative to said syringe body and said needle carrier, movement of said guide element along said longitudinal axis in a first direction toward said syringe body moving said plurality of axially projecting holding segment in a radial direction from a first position to a second position and movement of said guide element along said longitudinal axis in a second direction opposite said first direction moving said plurality of axially projecting holding segments from said second position to said first position; and a needle waste container having an opening and a structure adjacent said opening for engagement between the needle carrier and the syringe body, wherein the distal ends of said plurality of axially projecting holding segments are engaged with the inside surface of said needle carrier when said plurality of axially projecting holding segments are in said first position, and the distal ends of said plurality of axially projecting holding segments are disengaged from the inside surface of said needle carrier when said plurality of axially projecting holding segments are in said second position, said needle carrier and said needle are removable from said syringe body by moving said guide element to said first direction, inserting said needle carrier through the opening of said needle waste container, engaging said structure between said needle carrier and said syringe body, and axially retrieving said syringe body, said needle carrier and said needle separating from said syringe body and remaining in said needle waste container.

15. A method for connecting and releasing a needle from a reusable syringe comprising:

providing a reusable syringe body having a longitudinal axis, a front end defining an opening into which the needle can be inserted along said longitudinal axis, and a plurality of axially projecting holding segments arranged around said opening having threaded distal ends, said plurality of axially projecting holding segments being movable in a radial direction;

providing the needle in a needle carrier, the needle carrier having a threaded inside surface;

providing a guide element surrounding said plurality of axially projecting holding segments and axially movable relative to said syringe body and said needle carrier, movement of said guide element along said longitudinal axis in a first direction toward said reusable syringe body moving said plurality of axially projecting holding segments in a first radial direction and movement of said guide element along said longitudinal axis in a second direction opposite said first direction moving said plurality of axially projecting holding segments in a second radial direction opposite said first radial direction;

screwing the needle carrier onto the distal ends of said plurality of axially projecting holding segments;

moving said guide element along said longitudinal axis in said first direction to move said plurality of axially projecting holding segments in said first radial direction to disengage said threaded distal ends from said needle carrier, and pulling the needle carrier from the reusable syringe body.

* * * * *